United States Patent [19]

Parisius et al.

[11] Patent Number: 4,797,213

[45] Date of Patent: Jan. 10, 1989

[54] SEPARATION OF ISLETS OF LANGERHANS

[76] Inventors: John W. Parisius, 205 Maplehurst Avenue, Willowdale, Ontario, Canada, M2N 3C3; Anthony M. Sun, 4 Barkwood Crescent, Willowdale, Ontario, Canada, M2H 3G6

[21] Appl. No.: 17,844

[22] Filed: Feb. 24, 1987

[30] Foreign Application Priority Data

Feb. 24, 1986 [GB] United Kingdom ................ 8604497

[51] Int. Cl.⁴ ............................................. B01D 13/00
[52] U.S. Cl. .................................... 210/651; 210/768; 210/772; 210/335
[58] Field of Search ...................... 210/772, 768, 323.1, 210/335, 651; 435/240.21, 240.23; 424/104; 30/220; 83/408

[56] References Cited

U.S. PATENT DOCUMENTS

| | | | |
|---|---|---|---|
| 3,934,340 | 1/1976 | Jones et al. | 30/220 |
| 4,205,570 | 6/1980 | Soodalter | 83/408 X |
| 4,332,893 | 6/1982 | Rosenberg | 435/240.4 X |
| 4,477,567 | 10/1984 | Healy et al. | 435/240.23 X |
| 4,663,087 | 5/1987 | Jensen | 424/104 X |

Primary Examiner—Frank Spear
Attorney, Agent, or Firm—Sim & McBurney

[57] ABSTRACT

A semi-automated procedure for the isolation of Islets from the pancreata of different species is described. Pancreatic tissue first is treated to free the Islets from other pancreatic tissue. Enzyme digestion generally is used at least partially to achieve this effect. After separation of the Islet suspension from pancreatic debris, the suspension is subjected to multiple filtration to separate the Islets, which then are recovered from the filter.

9 Claims, 6 Drawing Sheets

SEPARATION OF ISLETS OF LANGERHANS

FIELD OF INVENTION

The present invention is directed to novel method and apparatus for the separation of Islets of Langerhans from pancreatic tissue, more particularly to a large scale and rapid recovery of such Islets from whole pancreas.

BACKGROUND TO THE INVENTION

The treatment of diabetes in humans, for the last sixty years, has relied on the daily injection of insulin recovered from the pancreatic tissue of cattle, pigs and occasionally sheep. More recently, human insulin, prepared either by chemical modification of porcine insulin or from fermentation of genetically-transformed *E. coli* cells has been used. In the last few years, transplantation of human pancreas has been attempted, but whilst the success rate has improved and a transplanted pancreas has remained operative for as long as two years, the process is still not considered reliable.

In U.S. Pat. No. 4,352,883 to Franklin Lim, there is described a method of encapsulating various cells, including Islets of Langerhans. This encapsulation procedure allows for the transplantation of the Islets into a mammal, with the Islets being able to react to circulating blood sugar levels and release insulin to control the disease, and yet not be subject to rejection phenomena. More recently, improvements have been made in the Lim process, as described in published European patent applications Nos. 0,127,713 and 0,127,989, assigned to the assignee hereof, such that microencapsulated Islets of Langerhans can survive and control blood sugar levels in a diabetic mammal for longer than one year. Such improvements have prepared the ground for experimentation with larger animals and, eventually, for clinical evaluation in humans as a treatment for diabetes.

Current procedures for the separation of Islets of Langerhans from an animal pancreas, for example, a calf pancreas, are carried out on a small scale by hand. The pancreas is cut into small pieces, the pancreatic tissue is contacted with collagenase in small tubes to digest some of the connective tissue and free the Islets, and the Islets are separated by centrifugation. This procedure requires repetitious treatments in order to separate the Islets cleanly from the pancreatic tissue debris. The operation is tedious since small volumes of materials only are being handled and often leads to death of many of the cells and a low overall yield of Islets.

The current Islet separation procedures are wholly inadequate to produce the volumes of Islets required for clinical evaluation of the microencapsulation process described in the above-mentioned patent and published applications. The present invention is directed to redressing this problem by providing method and apparatus for rapidly, effectively and essentially automatically processing pancreatic tissue to recover Islets.

SUMMARY OF INVENTION

In accordance with one aspect of the present invention, there is provided a method for the separation of Islets of Langerhans from pancreatic tissue, which comprises a multistep process. The first step of the process involves treating pancreatic tissue to release Islets from other pancreatic tissue and to provide an aqueous suspension Islets and pancreatic tissue debris.

The specific treatment operation which is effected in the first step depends on the animal source from which the pancreas is taken. In the case of the pancreas from bovine and rat sources, there is a specific membrane covering the Islets, which requires the use of enzyme digestion to free the Islets.

In the preferred treatment of pancreatic tissue wherein the Islets are covered by a membrane, the pancreatic tissue is first perfused with an enzyme solution, preferably collagenase solution, then is cut into thin slices and the sliced tissue is further digested in enzyme solution, again preferably collagenase solution, to dissolve some of the pancreatic tissue and free the Islets from extraneous connective tissue.

In the case of the pancreas from porcine and human sources, there is no specific membrane surrounding the Islets and extensive enzyme digestion then is not required. In the preferred treatment of such pancreatic tissue, the pancreas first is perfused with an enzyme solution, preferably collagenase solution, and, after a short time, is cut into a few large pieces. The large pieces then are passed through a physical macerator, preferably in the form of pairs of vertically-aligned intermeshing grooved rollers, which removes the Islets from the connective tissue by mechanical action.

The next step of the method is the removal of pancreatic tissue debris from the aqueous suspension. This separation step is most conveniently effected by screening the suspension using a coarse screen which permits the Islets to pass while retaining the debris.

The third step of the method of the invention is the subsequent removal of the Islets from the suspension. Again, this separation is most conveniently effected by screening. The screening preferably is effected using a plurality of filtration steps. The filtered Islets then are collected from the filter medium for future use.

In accordance with another aspect of the present invention, there is provided an apparatus for processing pancreatic tissue to recover Islets therefrom, comprising a plurality of elements. The first element is treatment means for releasing Islets from other pancreatic tissue and to provide an aqueous suspension of Islets and pancreatic tissue debris. In the case of bovine, rat and similar pancreata, the treatment means preferably comprises a digestion vessel having a first inlet for digestion enzyme solution, a second inlet for sliced pancreatic tissue to be digested, an outlet for liquid digest and a screen for retaining partially-digested pancreatic tissue while permitting freed Islets to pass out of the digestion vessel through the outlet. The screen located in the vessel functions as the first separation means in this structure. The digestion vessel preferably is lined with Velcro (trademark), which assists in trapping undigested pancreatic material in the vessel.

In the case of porcine, human and similar pancreata, the treatment means preferably comprises a macerator having an upper inlet for roughly chopped pancreatic tissue and a plurality of pairs of intermeshing grooved rollers arranged in a vertical stack, with the grooves progressing from coarser to finer from top to bottom. As the coarse mixture of pancreas and enzyme solution flows through the intermeshed rollers or gears, the pancreatic tissue is disrupted to finer and finer form. A screen acting as the first separation means is located in the macerator below the lowermost pair of rollers and above a lower outlet, so as to permit the separated Islets to pass out of the vessel and pancreatic debris to be retained.

In the macerator, the grooved rollers may have any desired dimension, typically each 2 inches in diameter, and may operate at any convenient speed, typically between 5 and 10 revolution per minute, preferably 8 rpm.

The second separation means preferably comprises a filter having a first inlet in fluid flow communication with the outlet from the digestion vessel or macerator, as the case may be, allowing receipt of the inlet suspension to the filter.

The filter preferably comprises a plurality of parallel filtration compartments separated one from another by filter elements positioned transverse to the path of flow of Islet suspension from the first inlet to a first outlet from the last of the compartments through which is discharged aqueous medium freed from Islets. The filter elements arrest the Islets on the surface thereof and preferably are of decreasing pore size in the direction of fluid flow through the filter from the first inlet to the first outlet.

The filter further includes a plurality of second inlets corresponding in number to the number of said filtration compartments and in fluid flow communication one with each of the filtration compartments, as well as a plurality of second outlets in fluid flow relationship with each of the filtration compartments. This structure permits wash fluid, for example, Hank's Basic Salt Solution, to pass through each of the filtration compartments from one of the second inlets to the corresponding one of the second outlets, across the face of the filter element in that compartment, so as to remove filtered Islets from each of the filtration compartments through the second outlet.

One or more collection vessels may be provided in communication with the second outlets from the filter to receive and collect Islets washed from the filter.

DESCRIPTION OF PREFERRED EMBODIMENT

In the present invention, pancreata from various sources may be processed to recover Islets, primarily bovine and porcine pancreata, but also including human pancreas.

Figure 1:
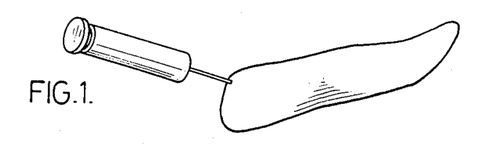
FIGS. 1 and 2 illustrate preliminary processing steps which may be effected on pancreatic tissue in this invention.

Pretreatment of the pancreas may be carried out, if desired, by perfusion of the whole pancreas with collagenase solution (FIGS. 1 and 2), cutting the perfused tissue into strips and removal of fat, membrane and connective tissue.

Figure 3:
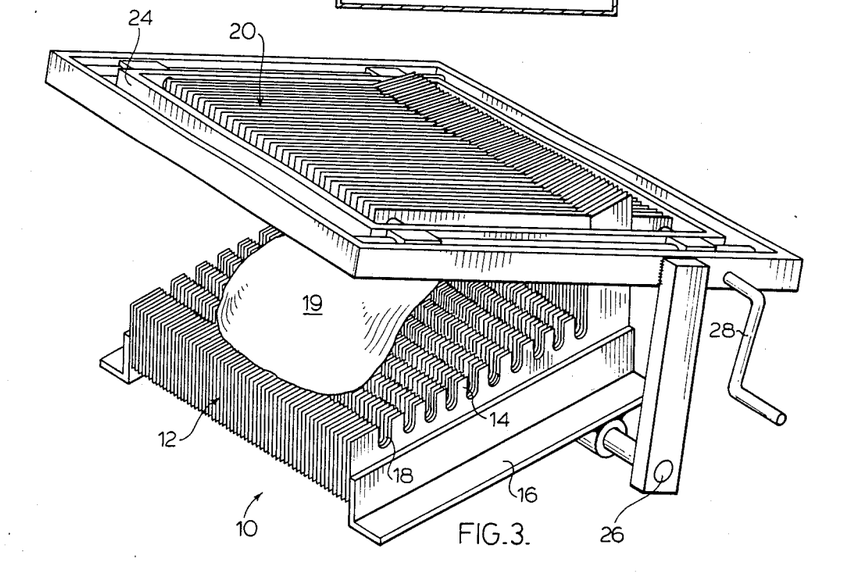
FIG. 3 is a perspective view of a slicer device useful for slicing up bovine pancreatic tissue for processing in the present invention.

The strips of pretreated tissue, or untreated tissue in strip or whole form, if desired, then is cut in preparation for digestion to release Islets. In effecting this cutting, it is desired to produce uniformly-thin tissue fragments with a minimum of damage. This result is difficult to achieve by hand, particularly when large volumes are to be processed. A novel tissue cutter has been developed to meet this requirement and is illustrated in FIG. 3. This novel cutter constitutes an additional aspect of the present invention.

The novel tissue cutter 10 comprises a lower bank 12 of individual steel plates 14 spaced apart from one another and horizontally mounted in a lower frame 16. The bank 12 of plates 14 has parallel transverse grooves 18 provided therein. The spacing between the steel plates 14 determines the thickness of the slice and typically may be 1.5 mm from centre to centre. The tissue cutter 10 may be sized to slice a single pancreas 19 or a plurality of pancreata, as desired. Typically, each groove 17 in the bank 12 is sized 9.5×19 mm.

Figure 2:
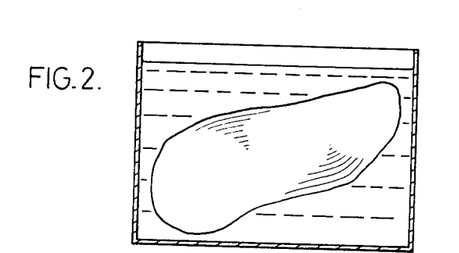

A bank 20 of individual cutting knives 22 spaced apart from one another is provided mounted in an upper frame 24 which is pivotally mounted via pivot rod 26 to the rear of the lower frame 16 for pivotal movement of the upper bank 20 of cutting knives relative to the lower bank 12 of plates 14. The cutting knives 22 typically also are spaced apart 1.5 mm from centre to centre and are arranged to interleave with the spaced-apart plates 14. A crank mechanism (the handle 28 of which is seen in FIG. 2) is provided in association with the upper frame 24 to permit the upper frame 24 to be moved back-and-forth relative to the lower frame 16 to slice up the tissue.

In using the cutter 10, the pancreatic tissue, typically initially sliced into 10 mm strips, is placed into the grooves 18 of the lower bank 12. The upper frame 24 then is slowly lowered by pivoting about pivot 26 while, at the same time, the upper frame 24 is moved back and forth, so that the knives 22 enter the gap between the plates 14 and uniformly slice the tissue.

Figure 4:
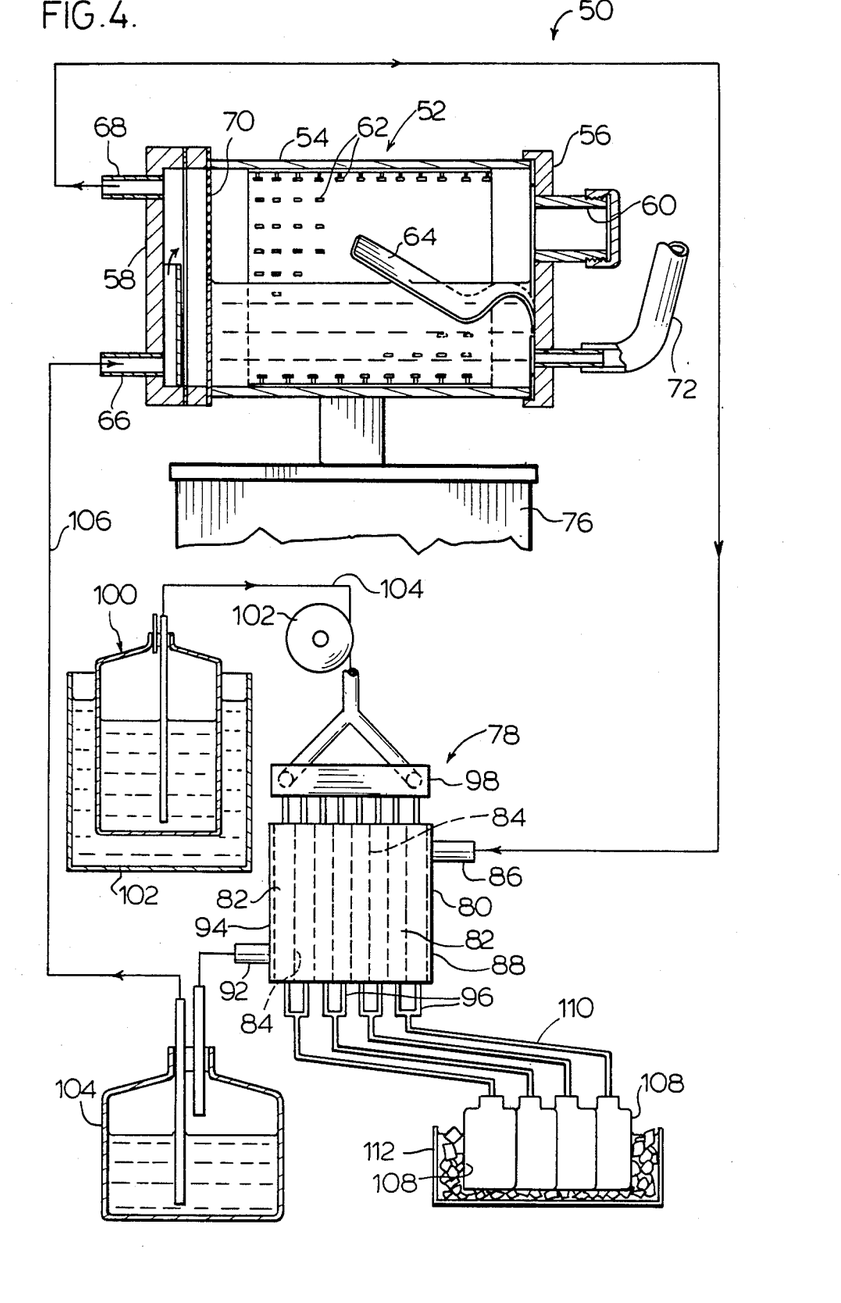
FIG. 4 is a diagrammatic view of pancreatic tissue processing apparatus for the processing of sliced bovine pancreatic tissue and provided in accordance with one embodiment of the invention.

The pancreatic tissue is now ready for further processing to separate Islets therefrom in apparatus 50 (see FIG. 4). The sliced tissue is placed in a digestion vessel 52, which comprises an elongate cylindrical body 54 having end closures 56 and 58. A tissue port 60 is provided in the end closure 56 for the introduction of the sliced tissue to the interior of the cylindrical body. A Velcro liner 62 is provided in the cylindrical body 54 for holding the residual tissue as the Islets are released. An agitator 64 is located in the vessel for agitation of tissue during digestion.

In the end closure 58, which forms the lower end of the digestion vessel 52 when the vessel is oriented to an upright position, there are provided a liquid inlet 66 for the introduction of recycled enzyme solution for digestion of the pancreatic tissue and a liquid outlet 68 for the drainage of liquid digest from the digestion vessel 52. A filter screen 70 is provided adjacent the lower closure 58 to permit separated Islets to pass therethrough while preventing unwanted tissue debris from passing out of the vessel 52 through the liquid outlet 68. An air vent 72 is provided in the upper closure 56.

An appropriate amount of enzyme solution, typically sterilized collagenase solution, is introduced to the digestion vessel 52 along with the pancreatic tissue. The digestion vessel 52 is mounted to a reciprocating shaker unit 76. The digestion vessel 52 is oriented horizontally during shaking, as shown, and usually at an angle to the shaking direction to ensure adequate agitation of contents of the digestion vessel.

The enzyme solution and pancreatic tissue are shaken, resulting in release of Islets from the connective tissue. The digestion usually is effected at a warm temperature, preferably about 37° C., to speed up the enzymatic digestion. The temperature may be maintained inside the vessel 52 by any convenient means, for example, by incubating the entire apparatus 50 at the desired temperature or by using a water-jacketed digestion vessel.

The digested material is drained from the vessel 52 through the outlet 68 by slowly tilting it from the horizontal orientation to the vertical orientation. Usually, a series of shakings of enzyme solution with pancreatic tissue followed by draining of the contents of the vessel 52 is effected, until all the tissue has been digested.

Figure 10:
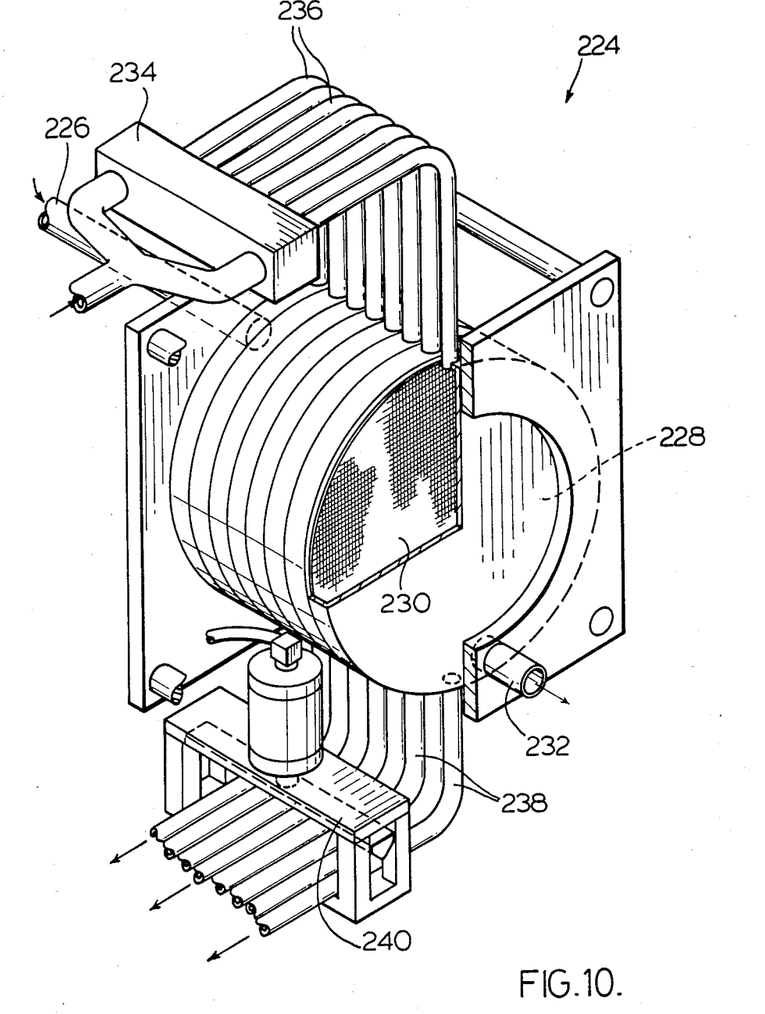
FIG. 10 is a perspective view of the filter device used in the apparatus of FIG. 7.

The digested material, comprising enzyme solution and released Islets, is passed from the digestion vessel 52 to a filter or sifting apparatus 78, which may be constructed as shown in detail in FIG. 10. The filter 78 comprises a hollow body 80 which is divided internally into eight parallel compartments 82 by filter elements 84. Although eight compartments 82 are illustrated, other numbers of such compartments may be employed, for example, four compartments.

A liquid digest inlet 86 communicates with the rightmost compartment 82 through end closure 88 and is connected by tubing to the liquid digest outlet 68 from the digestion vessel 52. An enzyme solution outlet 92 communicates with the left-most compartment 82 through another end closure 94.

The screens 84 usually are provided with decreasing pore size in the direction from right-hand most to left-hand most of the compartments. The actual screen openings employed depend on the size of the Islets to be filtered out, the coarsest typically ranging from about 150 to 250 microns and the finest typically being about 50 microns.

The filter 78 also has wash fluid inlets 95 communicating with each of the compartments 82 for introduction of wash fluid across the face of the screens 84. Drain outlets 96 also communicate with each of the compartments 82 for drainage of material eluted by the wash fluid from each compartment 82.

The wash liquid inlets 95 are connected to a common header 98 which communicates with a source of wash liquid 100 via a peristaltic pump 102 through line 104. The filter 78 is oriented with the digest inlet 86 vertical during receipt of digest from the digestion vessel 52 (i.e. with the unit rotated through 90° from the position seen in FIG. 4) and Islets are retained on the screens 84, as the enzyme solution percolates through the filter 78 to the enzyme solution outlet 92. To avoid any fat deposits in the compartments 82, the filter 78 usually is maintained at approximately the same temperature as that of the digestion vessel 52. This may be achieved, for example, by incubating the whole apparatus or by heating the washing fluid by immersing the wash fluid vessel 100 in a warm water bath 102. If the latter procedure is used, the enzyme solution, on its return to the digestion vessel 52, is passed through a heat exchanger to ensure that the desired digestion temperature is maintained.

After passing the left-most screen 84, the enzyme solution is removed from the filter 78 by outlet 92 to a storage vessel 104, from which the enzyme solution is recirculated to the digestion vessel 52 via line 106. To minimize losses, the filter 78 is passed through a series of movements to attempt to ensure that all fluid is drained from the filter 78 before washing of the screens 84 commences.

Following completion of the filtration step, the filter or sifter 78 is reoriented so that the liquid inlets 95 are oriented vertically and the digest inlet horizontal, as seen in FIG. 4. Wash fluid, e.g. Hank's Basic Salt Solution, from the storage tank 100 is introduced to the manifold 98 from where the wash fluid is distributed to the wash fluid inlets 95.

The wash fluid enters each of the compartments 82 through the inlets 95, passes across the face of the screens 84 to remove the Islets. The filter 78 may be shaken to free the Islets from the screen surface to facilitate their removal from the filter 78 in the wash medium. The wash fluid from each compartment 82 is drained through the respective outlets 96 to four separate collection bottles 108 via pipes 110. Adjacent pairs of the outlets 96 are joined to one of the pipes 110.

The collection bottles 108 are maintained at close to freezing temperature by standing them in an ice water bath 112. The collection bottles 108 contain some serum or other enzyme neutralizing agent. Usually, 5 to 10 shake-and-drain cycles of the digestion vessel are required to complete digestion of the tissue material from one pancreas, typically about 100 to 150 ccs in all. Once the cycles are complete, the contents of the collection vessels 108 are purified.

Typically, the purification may be effected by centrifuging the contents of the collection bottles 108 followed by further centrifugation of the sediment in a Ficoll density gradient. Following thorough washing of the purified Islets, they are reconstituted in culture medium. The viability of the collected Islets may be determined by testing with Trypan blue staining.

The various operations of the apparatus 50 may be effected automatically for each batch of sliced pancreatic tissue fed to the digestion vessel 52. The apparatus 50 is capable of rapidly processing pancreatic tissue to recover viable Islets. Typically, over 200,000 viable Islets can be recovered from a typical 100 cc batch of sliced bovine pancreatic tissue in a total cycle time of about 35 mins.

The apparatus described above with respect to FIGS. 1 to 4 is useful for recovering Islets from bovine, rat and similar pancreas containing membrane tissue. Enzyme digestion of membrane tissue is not necessary with other types of pancreas from which a membrane is absent, such as porcine and human pancreas. Gentler processing is required to separate Islets. Application of the procedure described above with respect to FIGS. 1 to 4 would result in complete disintegration of porcine pancreatic tissue into a suspension of single cells, rather than the desired discrete Islets.

Figure 5:
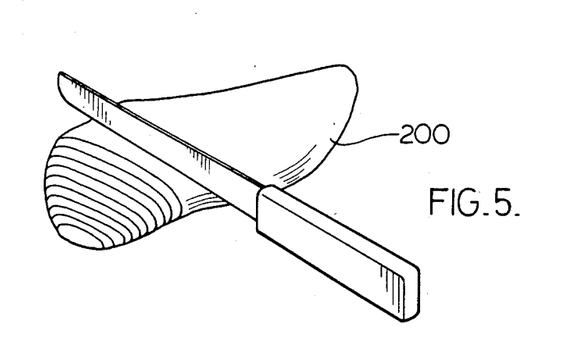
FIGS. 5 and 6 illustrate slicing up of porcine pancreatic tissue for processing in the present invention.
Figure 6:
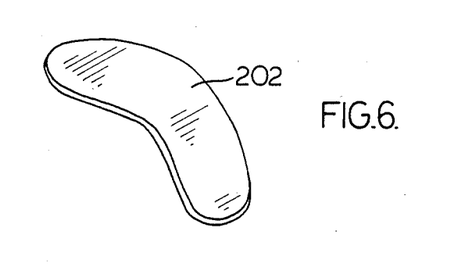

A procedure and apparatus for the processing of porcine and human pancreas to recover Islets therefrom are illustrated in FIGS. 5 to 10. Following preliminary processing of the pancreas by perfusion (FIGS. 1 and 2), the pancreas 200 is sliced by hand into relatively thick slices 202 (FIGS. 5 and 6). The thick slices 202 of pancreatic tissue then are passed to an Islet separation apparatus 204.

Figure 8:
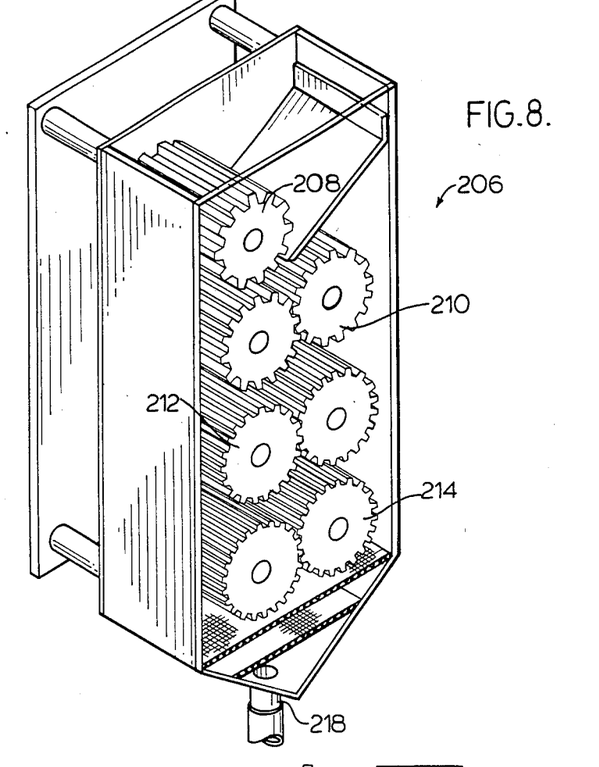
FIG. 8 is a perspective view of the macerator used in the apparatus of FIG. 7.

The pancreatic tissue slices 202 first are processed through a macerator 206. The macerator 206 possesses an upper feed roller 208 and three sets of rollers 210, 212 and 214, which have grooved surfaces which intermesh with each other. The roller sets have successively finer grooves from top to bottom. The rollers may be constructed of any suitable inert material, typically the polymer known by the trademark "Teflon" (polytetrafluoroethylene). The roller sets 210, 212 and 214 and the feed roller 208 are coupled through a drive chain 220 to be commonly driven by a motor 222. The macerator 206 is filled with a suitable aqueous medium for processing the tissue slices 202 therein. Passage through the increasing finer sets of rollers 210, 212 and 214 results in disruption of the tissue and the release of the Islets, leaving only connective tissue behind on coarse filter screens 216 located adjacent a lower outlet 218. The level of aqueous medium usually is lowered to the respective levels of the roller sets as the pancreas pieces pass each set.

Figure 7:
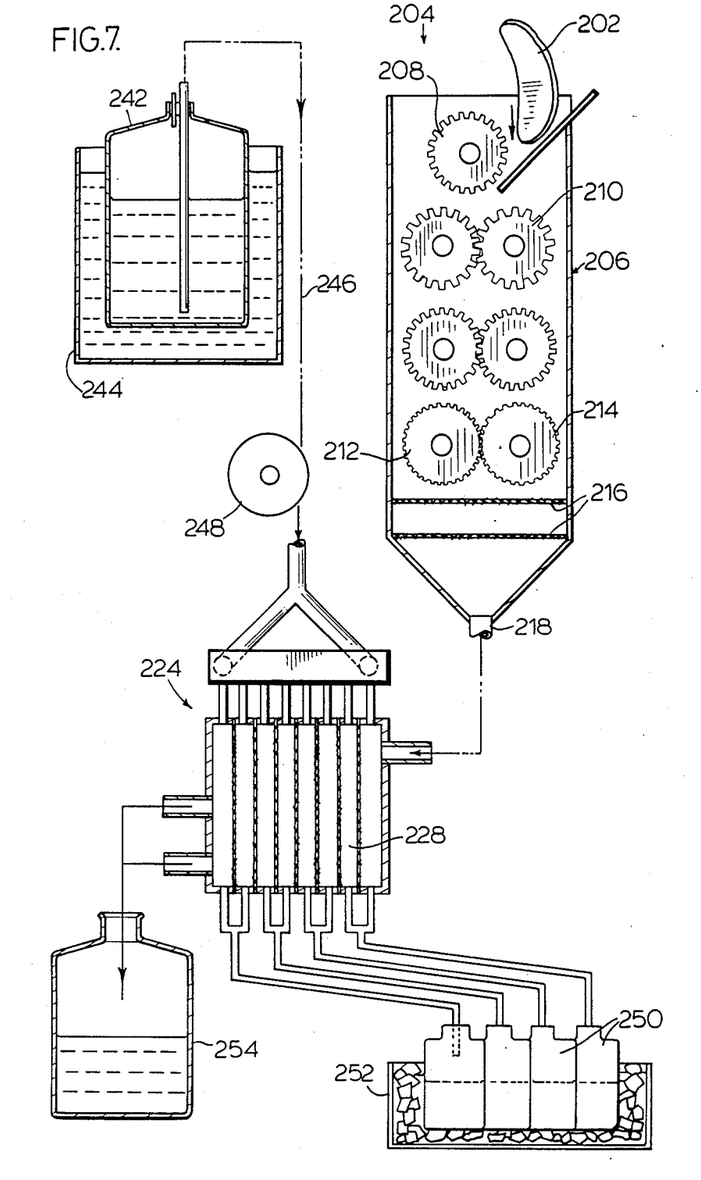
FIG. 7 is a diagrammatic view of a pancreatic tissue processing apparatus for the processing of sliced porcine pancreatic tissue and provided in accordance with another embodiment of the invention.

From the outlet 218 from the macerator 206, the Islets pass to a filter 224, which is constructed substantially as described above with reference to filter 78 in FIG. 4.

Further details of filter 224 are shown in Figure 10. As may be seen, an inlet 226 for Islet suspension communicates with a first of a plurality of compartments 228, each of which is separated from the next by a screen 230. The screens 230 have a decreasing pore size in the direction of flow of Islet suspension through the compartments 228 to a filtrate outlet 232. Typically, the pore size of the filter screens 230 ranges from about 500 to about 30 microns.

A wash fluid header 234 also communicates with each of the compartments 228 via pipes 236 and drain lines 238 also communicate with each of the compartments 228. Flow of liquid through the drain lines 238 may be selectively stopped by activation of a pneumatically-activated clamping mechanism 240.

The wash fluid header 234 is connected to a source of wash fluid 242 immersed in a water bath 244 through line 246. The flow of wash fluid from the source 242 to the header 234 is controlled by a peristaltic pump 248. The drain lines 238 are connected to collection bottles 250 immersed in an ice water bath 252.

The Islets in the Islet suspension entering the filter 224 are removed on the filter screens 230 with the filter 224 oriented through 90° from the orientation seen in FIGS. 7 and 20. The residual liquid from the filtration, now from from Islets, is passed out of the filter 224 by outlet 232 to a waste collection vessel 254.

Harvesting of the Islets from the filter 224 is effected in the same manner as is described above with respect to the embodiment of FIGS. 1 to 4 for the filter 78. Harvest material from two adjacent screens 230 is combined to provide four separate fractions, collected in the collection vessels 250. The Islets in these four fractions are purified as described above with respect to FIGS. 1 to 4.

The Islet separation method of the invention is clearly superior to the conventional separation procedure, in that large quantities of viable Islets can be recovered from pancreatic tissue in a rapid procedure in a semi-automated manner.

EXAMPLES

Example I

Calf pancreata obtained from three- to four-month old animals (approximately 300 lbs) were obtained from the local slaughter house. They were collected at the point where the viscera is separated from the carcass, by which time the animal had been dead for approximately 25 minutes. The pancreas was placed in cold Dakin's (see Parker "Methods of Tissue Culture") solution for fifteen minutes and the medium then was changed over to cold transport medium (Hank's B.S.S. (pH 7.2, 0.05% glucose) containing 10% adult bovine serum and 100 units/ml of Aprotinin). This transfer of tissue from one medium to another was made during the transport of the pancreas from abbatoir to laboratory.

The pancreas was warmed for approximately 10 minutes in warm-up and washing medium (this is, transport medium, but without serum and Aprotinin) before it was perfused, via the duct, with 150 ml of collagenase solution at a rate of 10 ml/minute. The enzyme solution was prepared by dissolving 5 g of Sigma Type V collagenase in 500 ml of warm-up and washing medium and the solution sterilised by passing twice through the same 0.45 micron membrane filter (Pall, Ultipor DFA30-01ACP) and 10% of sterile, adult bovine serum was added. The temperature of the pancreas and solution during this phase varied between 30° and 35° C.

The pancreas then was cut into approximately 10 mm strips from which fat, membrane and connective tissue were removed as much as possible. The strips were then placed into the slicer illustrated in FIGS. 1 and 2 and cut into thin slices. As a result of the predigestion of the pancreas by enzyme solution, no discreet slices were obtained. Using a pair of forceps, the tissue was gathered into a flask containing 300 ml of warm (about 37° C.) collagenase solution. The tissue collected represented approximately 100 ml of original material. The solution was placed in the digestion vessel of FIG. 3 for commencement of the Islet digestion and separation cycle. In the digestion vessel, the tissue was subjected to 90 seconds of stirring, interrupted by 2 seconds of shaking every 15 seconds. This was then followed by 2 minutes of continuous shaking and finally a 30 second period of draining. This procedure was repeated automatically until the tissue was digested.

In the filter of FIG. 5, screens sized 250, 150, 115 and 53 microns were used for the bovine pancreas. The digest from the digestion vessel, comprising a suspension of Islets in enzyme solution, was passed to the filter and through the screens to remove suspended matter. After carefully draining all residual fluid, the enzyme solution, freed of Islets by the filtration, was recycled to the digestion vessel for utilization in the next cycle.

The screens then were washed with Hank's B.S.S. and then using a second portion of the washing medium the filter was shaken for 20 seconds to dislodge the deposit on the screens. The eluate from the four screens was collected separately in four bottles. Most of the Islets were found in Fractions 1, 2 and 3.

The harvests were centrifuged and the sediments were separately subjected to Ficoll density gradient centrifugation using concentrations of 25, 23, 20 and 11%. After thorough washing, the Islets were reconstituted in culture medium and samples of a suitable dilution were counted under the microscope. Viability of the Islets was demonstrated by Trypan blue staining.

The yields from four different experiments were determined and are tabulated in the following Table:

TABLE

| Expt No. | Fraction No. | Islets/Fraction ($\times 10^3$) | Total No. Islets/run* ($\times 10^3$) |
|---|---|---|---|
| 1 | 1 | 62 | 234 |
|   | 2 | 80 |   |

TABLE-continued

| Expt No. | Fraction No. | Islets/Fraction (× 10³) | Total No. Islets/run* (× 10³) |
|---|---|---|---|
|  | 3 | 76 |  |
|  | 4 | 16 |  |
| 2 | 1 | 104 | 362 |
|  | 2 | 80 |  |
|  | 3 | 114 |  |
|  | 4 | 64 |  |
| 3 | 1 | 64 | 232 |
|  | 2 | 76 |  |
|  | 3 | 72 |  |
|  | 4 | 20 |  |
| 4 | 1 | 24 | 152 |
|  | 2 | 56 |  |
|  | 3 | 64 |  |
|  | 4 | 8 |  |
| Average Yield | 1 | 64 | 245 |
|  | 2 | 73 |  |
|  | 3 | 82 |  |
|  | 4 | 27 |  |

Note:
*Total of Fractions 1 to 4
As may be seen from this Table, large numbers of viable Islets can be collected from a calf pancreas in a short time cycle (total cycle time was 36 minutes).

Example II

Pancreata from 6 to 7 month old hogs, weighing approximately 175 lbs., were obtained from a local slaughter house. At the time of removal of the pancreas, the animals had been dead approximately 23 to 25 minutes. During this period, the carcass had been exposed to the scalding tank at 60° C. for 8 minutes, which raises the inner temperature of the animal approximately 2° C. After the pancreas had been excised, it was first immersed for approximately 2 minutes in cold Dakin's solution (see Example I above) and then placed into ice-cooled transport medium (as Example I above but without Aprotinin) for transport to the laboratory.

After removing exterior fat and connective tissue, the pancreatic duct was canulated and the organ was placed in warm (37° C.) Hank's B.S.S. solution. The pancreas then was rapidly extended (about 3 to 5 minutes duration) with 200 ml of prewarmed enzyme solution. The enzyme solution was made by dissolving 150 mg of Sigma Type XI collagenase in 200 ml of transport medium. After a total incubation time of about 10 to 12 minutes, as determined by the degree of softness of the tissue, the pancreas was cut into a few large pieces and fed into the macerator illustrated in FIG. 8.

Prior to use, the macerator was filled with warm (37° C.) Hank's solution to the level of the upper set of gears or rollers. With the gears in the macerator running, the tissue was fed into the apparatus. When the tissue had cleared the first set of gears, the liquid level was lowered to the second set and when these had been cleared, to the third set. The apparatus then was allowed to drain and was rinsed with a small volume of buffer. Two screens (1500 and 100 micron pore size) at the bottom of the apparatus, located above the outlet, retained undigested and connective tissue.

Figure 9:
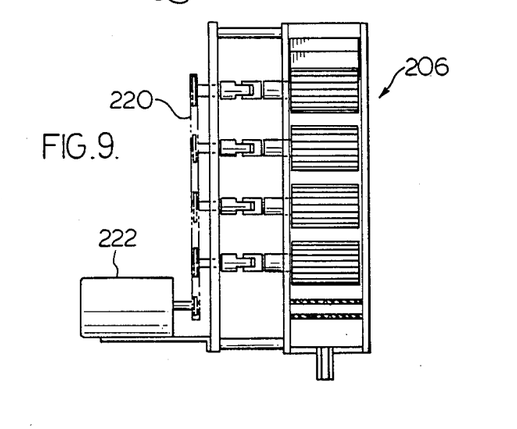
FIG. 9 is an end view of the macerator of Figure 9.

The macerator was connected to the filter having the configuration of FIG. 9 and the tissue/islet suspension was flowed through the filter compartments by gravity, with the effluent being discarded. The material retained by the screens was washed and eluted (twice) with warm buffer solution and the harvest collected in 4 ice-cooled bottles containing serum or other enzyme neutralizing agents. The total cycle time from tissue disruption to collection was under five minutes. The harvested material was centrifuged and purified as described in Example 1.

SUMMARY OF DISCLOSURE

In summary of this disclosure, the present invention provides a novel method and apparatus for processing pancreas tissue to collect large volumes of viable Islets. Modifications are possible within the scope of this invention.

We claim:

1. A method for the separation of Islets of Langerhans from pancreatic tissue, which comprises:
   treating pancreatic tissue to release Islets from other pancreatic tissue to provide an aqueous suspension of Islets and pancreatic tissue debris;
   removing said pancreatic tissue debris from said aqueous suspension by filtering off said pancreatic tissue debris and leaving an aqueous suspension of Islets,
   removing said Islets from said aqueous suspension by passing said aqueous suspension of Islets successively through a series of screens of decreasing pore size in the direction of flow of said suspension of Islets so as to remove said Islets from said aqueous suspension of Islets on the surface of said screens, and
   recovering the Islets from each of said screen surfaces by passing an aqueous wash medium across the surface of each of the screens to remove said Islets from said screen surfaces as an aqueous suspension thereof in said aqueous wash medium.

2. The method of claim 1 wherein said pancreatic tissue is bovine or rat pancreatic tissue and said treatment includes enzymatic digestion.

3. The method of claim 1 wherein said pancreatic tissue is porcine or human pancreatic tissue and said treatment includes maceration.

4. A method of separation of Islets of Langerhans from bovine or rat pancreatic tissue, which comprises:
   agitating thin slices of said pancreatic tissue in enzyme solution capable of digestion of pancreatic membrane tissue for a tissue sufficient to release said Islets from said pancreatic tissue, to provide a digest suspension of pancreatic tissue debris Islets,
   filtering out said pancreatic tissue debris from said Islet suspension, and
   passing the resulting Islet suspension through a series of filter screens of decreasing pore size to filter out Islets from said suspension on said screens to provide an Islet-free digest solution which is recycled to said agitation step, and
   washing said Islets from said filter screens by passing in aqueous wash medium across the surface of each screen and collecting the washed Islets.

5. A method of separation of Islets of Langerhans from porcine or human pancreatic tissue, which comprises:
   macerating strips of said pancreatic tissue in an aqueous medium for a time sufficient to release said Islets from said pancreatic tissue to provide a suspension of pancreatic tissue debris and Islets,
   filtering out said pancreatic tissue debris from said Islet suspension,
   passing the resulting Islet suspension through a series of filter screens of decreasing pore size to filter out Islets from said suspension on said screens to provide an Islet-free aqueous medium for discard, and washing said Islets from said filter screens by passing an aqueous wash medium across the surface of each screen and collecting the washed Islets.

6. A pancreatic cutting tissue apparatus, comprising:

lower horizontal cutting surface means comprising a first plurality of parallel closely-spaced upright thin metal strips mounted in a first frame member, said lower cutting surface means having a plurality of upwardly-opening parallel grooves formed in said first plurality of metal strips and extending transverse to the direction of extension of said strips, upper cutting surface means comprising a second plurality of closely-spaced upright thin metal strips mounted in a second frame member pivotally connected to said first member and movable to a cutting position wherein said second plurality of metal strips are at least partially interleaved with said first plurality of metal strips, and means associated with said upper cutting surface for reciprocating said second plurality of metal strips in said second frame member so that said second plurality of metal strips move reciprocably longitudinally relative to said first plurality of metal strips in said cutting position so as to cut pancreatic tissue into thin slices.

7. An apparatus for the separation of Islets of Langerhans from pancreatic tissue, which comprises:

treatment means for releasing Islets from other pancreatic tissue and to provide an aqueous suspension of Islets and pancreatic tissue debris;

first separation means for removing pancreatic tissue debris from said aqueous suspension; and second separation means for removing Islets from said aqueous suspension, said second separation means comprising filter means, said filter means comprising:

a plurality of parallel filtration compartments separated from one another by filter elements, said filter elements in said compartments having a decreasing pore size from a first filtration compartment to a last filtration compartment, a first inlet to said first filtration compartment in fluid flow communication with an outlet from said first separation means to receive said aqueous suspension of Islets from said first separation means, a first outlet from said last filtration compartment so as to establish a path of flow of said Islet suspension from said first inlet to said first outlet and to arrest Islets on the surface of said filter elements, and a plurality of second inlets and a plurality of second outlets corresponding in number to the number of said compartments and arranged in fluid flow communication with each of said compartments to permit, in such compartment, wash liquid to flow from one of said second inlets to one of said second outlets across the surface of the filter element to wash filtered Islets therefrom and out of the filter means through the corresponding one of said second outlets.

8. The apparatus of claim 7 wherein said treatment means comprises a digestion vessel having a first inlet for digestion enzyme solution, a second inlet for sliced pancreatic tissue to be digested and an outlet for liquid digest, and said first separation means comprises a screen positioned in said vessel to retain partially-digested pancreatic tissue while permitting freed Islets to pass out of the digestion vessel through the outlet.

9. The apparatus of claim 7 wherein said treatment means comprises a macerator having an upper inlet for roughly chopped pancreatic tissue, a plurality of pairs of intermeshing grooved rollers arranged in a vertical stack, with the grooves progressing from coarser to a finer from top to bottom and a lower outlet for separated Islets, and said first separation means comprises a screen positioned in said vessel to retain pancreatic tissue debris while permitting freed Islets to pass out of the macerator through the outlet

* * * * *